(12) United States Patent
Borghi

(10) Patent No.: US 6,736,824 B2
(45) Date of Patent: May 18, 2004

(54) APPARATUS AND METHOD FOR ANASTOMOSIS

(75) Inventor: Enzo Borghi, Budrio (IT)

(73) Assignee: I. & S. Idee & Sviluppo S.R.L., Bologna (IT)

( * ) Notice: Subject to any disclaimer, the term of this patent is extended or adjusted under 35 U.S.C. 154(b) by 32 days.

(21) Appl. No.: 09/979,282

(22) PCT Filed: Mar. 26, 2001

(86) PCT No.: PCT/IB01/00490

§ 371 (c)(1),
(2), (4) Date: Nov. 20, 2001

(87) PCT Pub. No.: WO01/72232

PCT Pub. Date: Oct. 4, 2001

(65) Prior Publication Data

US 2003/0088255 A1 May 8, 2003

(51) Int. Cl.⁷ .............................................. A61B 17/04

(52) U.S. Cl. ................................................... 606/153

(58) Field of Search .............................. 606/153, 213, 606/216, 217, 139, 148, 151

(56) References Cited

U.S. PATENT DOCUMENTS

| | | | | |
|---|---|---|---|---|
| 3,254,650 A | * | 6/1966 | Collito | 606/153 |
| 4,214,586 A | | 7/1980 | Mericle | |
| 4,233,981 A | * | 11/1980 | Schomacher | 606/153 |
| 4,523,592 A | * | 6/1985 | Daniel | 606/153 |
| 4,747,407 A | * | 5/1988 | Liu et al. | 606/153 |
| 4,766,898 A | | 8/1988 | Hardy et al. | |
| 5,089,008 A | | 2/1992 | Chen | |
| 5,089,014 A | | 2/1992 | Holfert | |
| 5,123,908 A | | 6/1992 | Chen | |
| 5,250,058 A | | 10/1993 | Miller et al. | |
| 5,457,141 A | | 10/1995 | Matsuda et al. | |
| 6,030,392 A | | 2/2000 | Dakov | |

\* cited by examiner

*Primary Examiner*—Gary Jackson
(74) *Attorney, Agent, or Firm*—Fay, Sharpe, Fagan, Minnich & McKee, LLP

(57) ABSTRACT

An apparatus and method for anastomosis between two free end edges (6, 7) of respective separate end portions (4, 5) of a vessel (3) or of a duct (3), according to which a connecting element (11, 24) is attached and fixed to each end portion (4, 5) so that the connecting element engages the end portion (4, 5) with the exception of the free end edge (6, 7); the connecting elements (11, 24) are then connected and fixed to one another in a mutual connection position (P) in which the end edges (6, 7) meet in a configuration of close and total reciprocal contact.

20 Claims, 5 Drawing Sheets

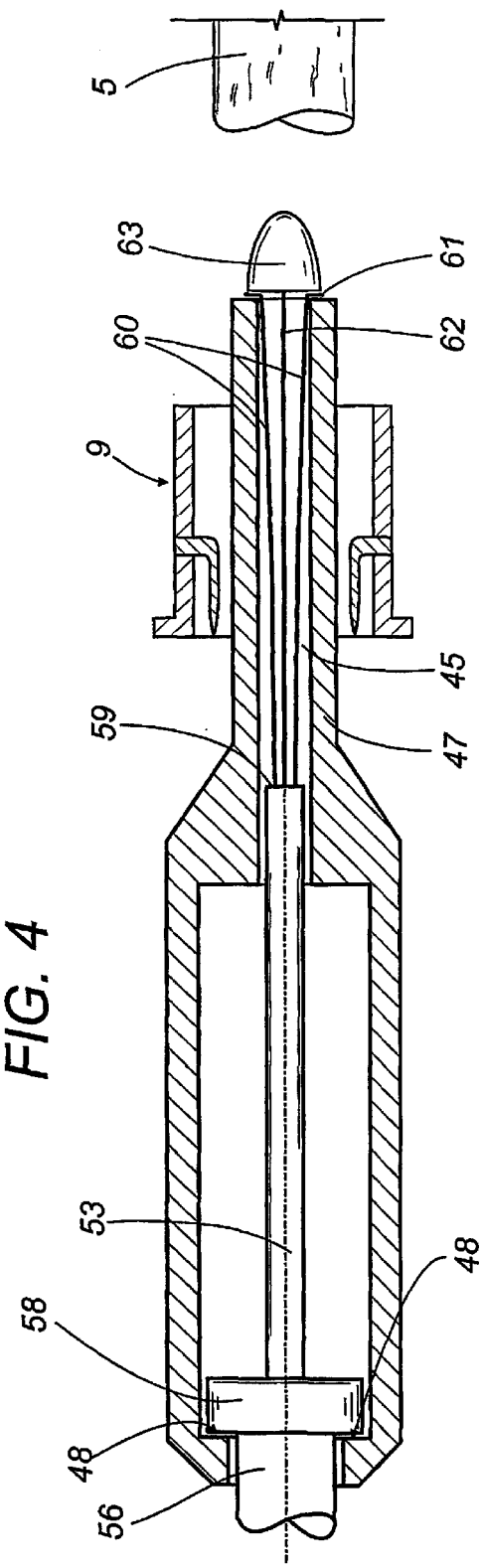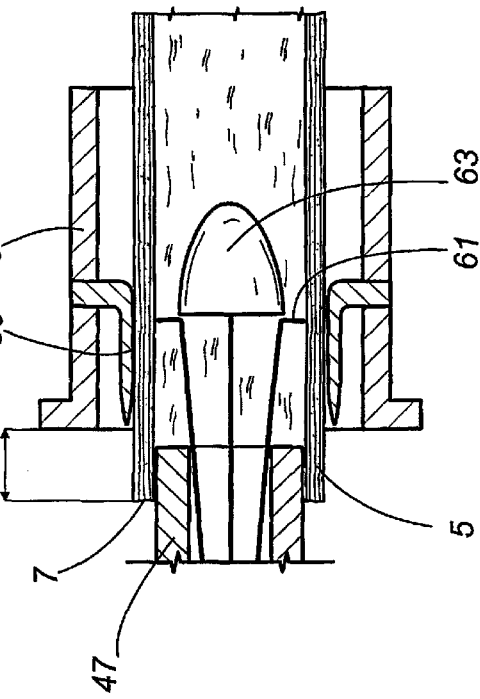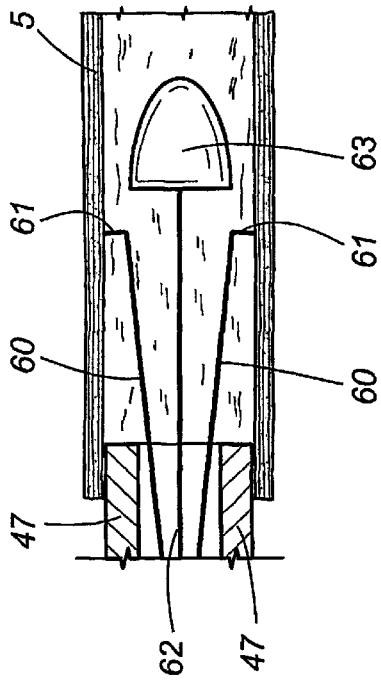

APPARATUS AND METHOD FOR ANASTOMOSIS

TECHNICAL FIELD

The present invention relates to an apparatus and method for anastomosis.

BACKGROUND ART

In surgical techniques, the term anastomosis means the connection of organs or histological elements.

In particular, where said connection is between two portions of a blood vessel, a lymph vessel or other type of duct, specific reference is made to end anastomosis, referring to an end-to-end connection between the two portions, in order to restore the original continuity of the above-mentioned vessel or duct.

In the description which follows, specific reference is made to end-to-end vascular anastomosis applied to the human body, although without limiting the scope of application of the invention.

A known technique for anastomosis of two portions of a blood or lymph vessel consists in suturing the free flaps of the portions.

A similar technique, commonly known as suture anastomosis, has various disadvantages.

A first disadvantage is the fact that, since the suture creates more or less marked scarring of the vessel upon which the surgery is performed, it does not perfectly restore the original continuity of the vessel.

On this subject, it must be emphasised that, as is known, blood vessels have a multi-layer structure, in which a first inner layer, called the endothelium of the tunica intima, is covered by a second, middle layer, called the tunica intima. The tunica intima is, in turn covered, by means of an elastic membrane, by a third middle layer, called the tunica media.

The tunica media is covered, by means of an elastic membrane, by a fourth middle layer, called the tunica adventitia, which is in turn coated, by means of a fifth layer of feeding vessels, by a sixth, external layer called the wall nerve.

It is, therefore, evident that suturing the flaps normally results in a more or less accentuated misalignment of the above-mentioned layers of one flap and the corresponding layers of the other flap. This disadvantage also arises in the case of lymph vessels, which also have a multi-layer structure.

A second disadvantage is the fact that the flaps must be sutured manually by a surgeon, since this complex operation cannot be entrusted to a robot.

Another known technique for anastomosis of two portions of a blood or lymph vessel consists of using special mechanical locking devices designed to fix the above-mentioned flaps together.

A similar type of anastomosis, commonly known as mechanical anastomosis, normally involves everting the flaps of the portions to be joined, bringing together the inner layers of the everted flaps and fixing the flaps together by means of the above-mentioned mechanical locking devices, which operate upon the outer layers of the flaps.

Mechanical anastomosis performed as described above, normally known as mechanical anastomosis by eversion, is more simple than suture anastomosis, but, in contrast to the latter, does not restore the original continuity of the vessel at all.

For example, in the specific case of blood vessels, it is evident that the layers over the endothelium of the tunica intima of one flap remain isolated from the corresponding layers over the endothelium of the tunica intima of the other flap.

Moreover, mechanical anastomosis by eversion has further serious disadvantages which mean that it endangers the health of the patient.

A first disadvantage is the fact that the operation in which the flaps are everted may result in rupture of the flaps themselves, particularly in the case of vessels with a large diameter, such as arteries.

Another disadvantage, specific to blood vessels, is the fact that the inner layers of the flaps which are everted and which have been brought together are no longer supplied with blood and tend to atrophy, resulting in serious complaints for the patient. This disadvantage in particular is more acutely felt as the diameter of the vessel operated upon gets smaller.

DISCLOSURE OF THE INVENTION

The aim of the present invention is to provide an apparatus for anastomosis which is free of the disadvantages indicated with reference to the background art.

Accordingly, the present invention provides an apparatus for anastomosis between a first and a second part of a vessel or duct, said first and second parts respectively having a first and a second end portion delimited by free end edges. The apparatus is characterised in that it comprises first connecting means which are shaped and may be positioned on the first end portion in order to engage the first end portion with the exception of the free end edge, second connecting means which are shaped and may be positioned on the second end portion in order to engage the second end portion with the exception of the free end edge, and connecting means for connecting and fixing together the first and second connecting means in a position in which they are attached to one another and in which the end edges meet in a configuration of close and total reciprocal contact.

Another aim of the present invention is to provide a method for anastomosis which is free of the disadvantages mentioned with reference to the background art.

Accordingly, the present invention provides a method for anastomosis between a first and a second part of a vessel or duct, said first and second parts respectively having a first and a second end portion delimited by free end edges. The method is characterised in that it comprises a step of connecting the first and second connecting means to the first and second end portions. Said connecting means are shaped and may be positioned on the first and, respectively, the second end portion in order to engage the first and, respectively, second end portion with the exception of the free end edge; and connecting and fixing together the first and second connecting means in a position in which they are attached to one another and in which the end edges meet in a configuration of close and total reciprocal contact.

The present invention is now described with reference to the accompanying drawings, which illustrate a preferred embodiment of it without limiting the scope of its application, and in which:

FIG. 4 illustrates a detail from FIG. 3, in a first operating moment;

FIG. 5 illustrates a detail from FIG. 3, in a second operating moment;

FIG. 6 illustrates a detail from FIG. 3, in a third operating moment;

Figure 1:
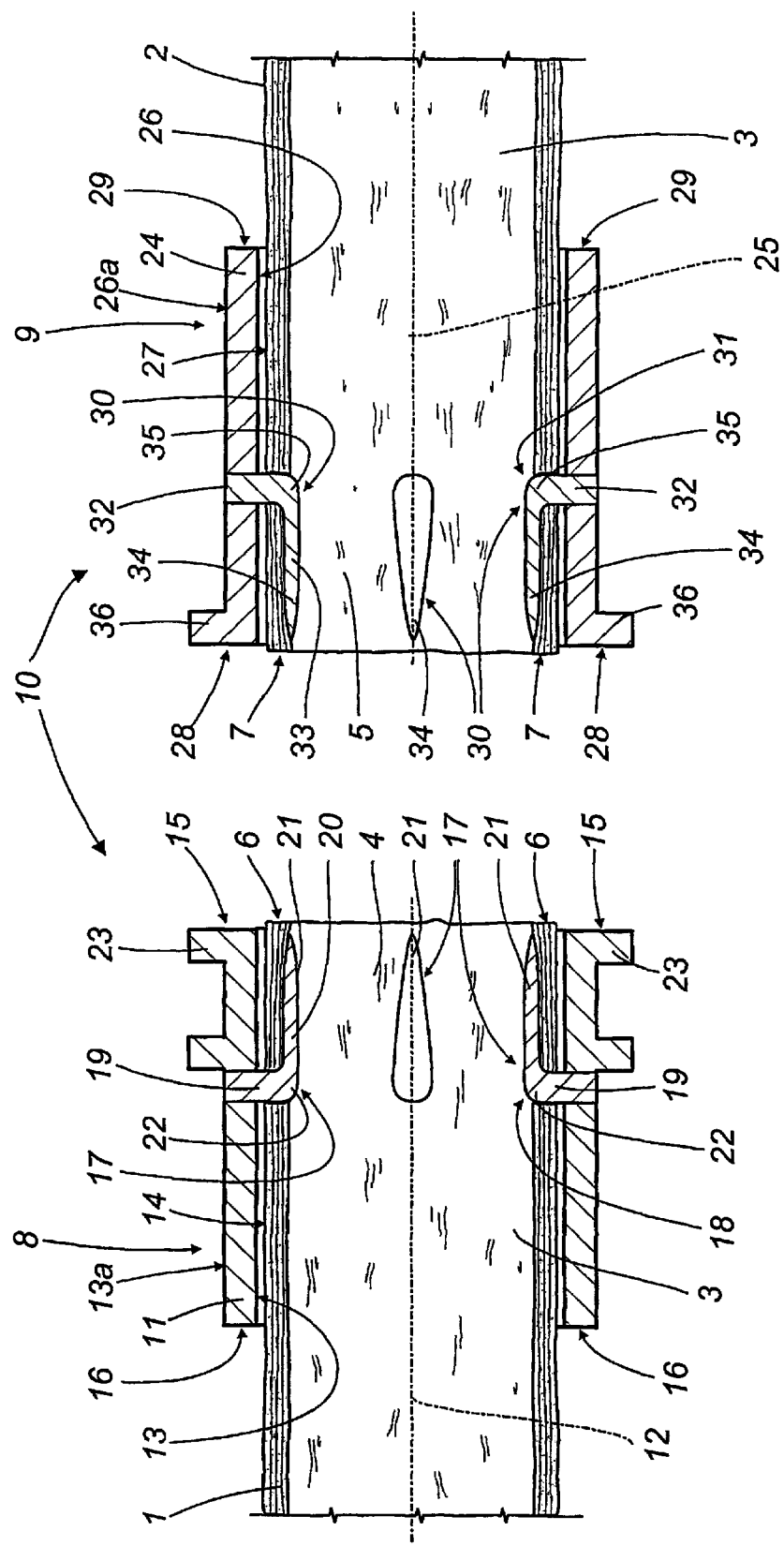
FIG. 1 is a schematic view with some parts in cross-section and some parts cut away for greater clarity, of an embodiment of a portion of the apparatus made in accordance with the present invention, in a first operating configuration.

With reference to FIG. 1, the numerals 1 and 2 denote a first and a second part of a blood or lymph vessel 3.

The parts 1 and 2 respectively have a first and a second end portion 4, 5, each longitudinally delimited by its own free end edge 6, 7 which is ring-shaped and substantially circular.

The numerals 8 and 9 indicate two connecting elements, which may be attached, respectively, to the portions 4 and 5 forming two elements which may be connected to one another of an anastomosis apparatus labelled 10 as a whole.

The element 8 comprises a tubular body 11, extending symmetrically about a central axis 12 and delimited inside and outside by cylindrical surfaces 13, 13a.

The inner surface 13 has a diameter that is just slightly greater than the outer diameter of the portion 4 and is designed to make close contact with the outer surface 14 of the portion 4.

The body 11 is axially delimited by two circular ring-shaped edges 15, 16 and supports a plurality of fixing hooks 17 between them. The hooks are evenly distributed in a ring-shape in the body 11 along a ring-shaped middle portion 18 of the inner surface 13.

Each hook 17 has a first end 19 rigidly supported by the body 11, extending radially inside the body 11, a second end 20, opposite the first end 19, extending parallel with the axis 12, forming a point 21 which points towards the edge 15, and a curved portion 22 which connects the ends 19 and 20.

The end 20 is separated from the inner surface 13 by a distance which is just slightly greater than the thickness of the portion 4.

The body 11 also has an outer circular flange 23, which extends radially from the outer surface 13a flush with the edge 15.

Similarly to the element 8, the element 9 comprises a tubular body 24, extending symmetrically about a central axis 25 and delimited on the inside and outside by cylindrical surfaces 26, 26a.

The inner surface 26 has a diameter that is just slightly greater than the outer diameter of the portion 5 and is designed to make close contact with the outer surface 27 of the portion 5.

The body 24 is axially delimited by two circular ring-shaped edges 28, 29 and supports a plurality of fixing hooks 30 between them. The hooks are evenly distributed in a ring-shape in the body 24 along a ring-shaped middle portion 31 of the inner surface 26.

Each hook 30 has a first end 32 rigidly supported by the body 24, extending radially inside the body 24, a second end 33, opposite the first end 32, extending parallel with the axis 25, forming a point 34 which points towards the edge 28, and a curved portion 35 which connects the ends 32 and 33.

The end 33 is separated from the inner surface 26 by a distance which is greater than or equal to the thickness of the portion 5.

The body 24 also has an outer circular flange 36, which extends radially from the outer surface 26a flush with the edge 28.

The body 11 is designed for connection to the portion 4, with its edge 15 facing the edge 6, whilst the body 24 is designed for connection to the portion 5, with its edge 28 facing the edge 7.

Figure 2:
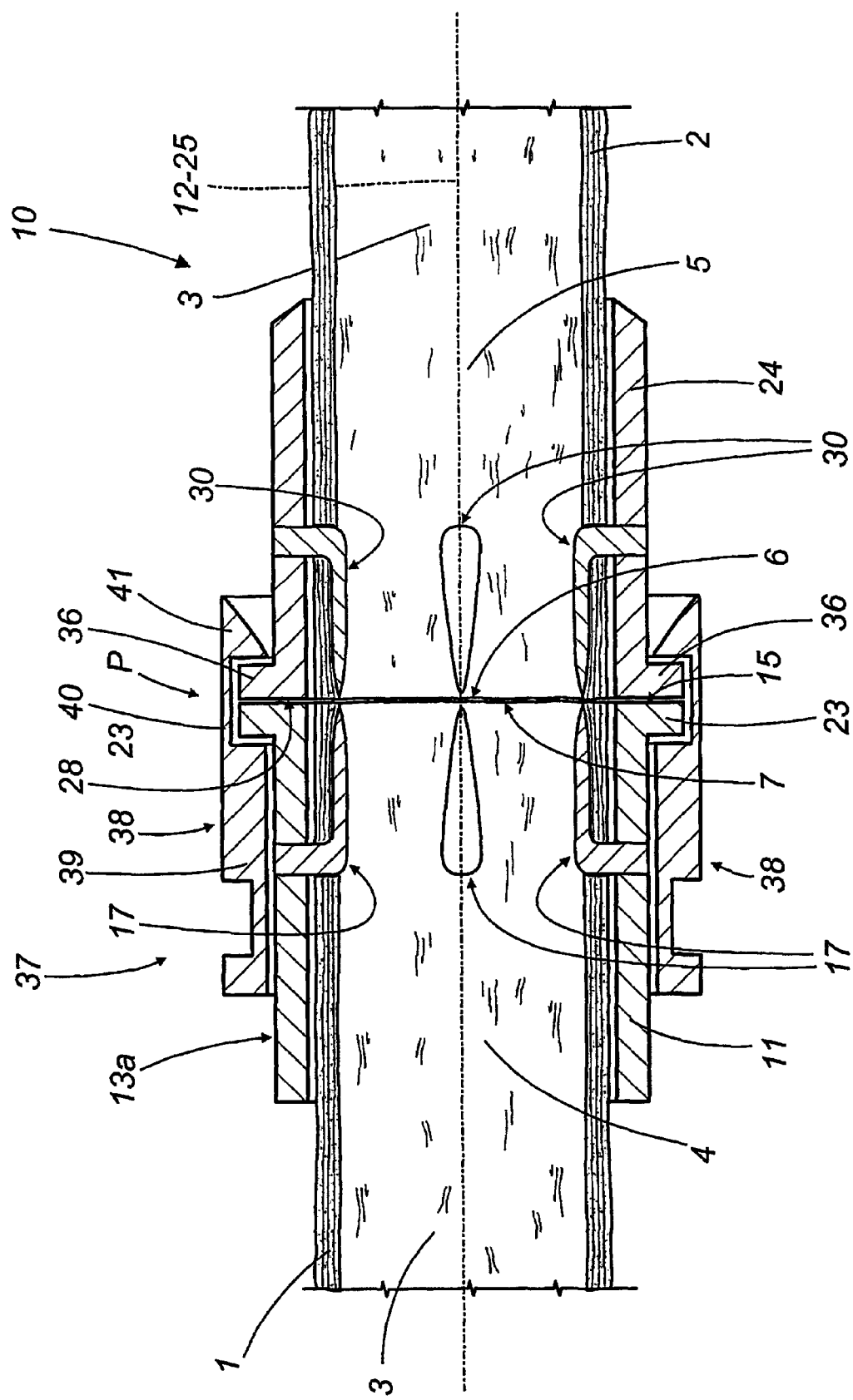
FIG. 2 is view of the portion illustrated in FIG. 1, in a second operating configuration.

As illustrated in FIG. 2, the edges 15 and 28 are also designed to be brought into contact with one another in a position P of mutual connection in which the edges 6 and 7 of the portions 4 and 5 meet in a configuration of close and total reciprocal contact.

For this purpose, the apparatus 10 comprises releasable locking means, labelled 37, designed to hold the flanges 23 and 36 in a reciprocal joining position in which the edges 15 and 28 make contact with one another in the above-mentioned position P.

The locking means 37 comprise an elastic locking coupling 38, pre-mounted on the body 11 close to the flange 23 and the outside of the body 11.

The coupling 38 elastically grips the outer surface 13a of the body 11 with a portion 39, from which a support tap 40 for a ring-shaped connecting tooth 41 extends axially. The tooth is also subject to elastic deformation and is designed to engage with the flange 36 in the above-mentioned flange 23 joining position.

The bodies 11 and 24, the hooks 17 and 30, the flanges 23 and 36, the coupling 38, the tab 40 and the tooth 41 are made of bio-compatible and bio-absorbable material.

Moreover, the bodies 11 and 24 and the flanges 23 and 36 are preferably made of an elastic material.

Figure 3:
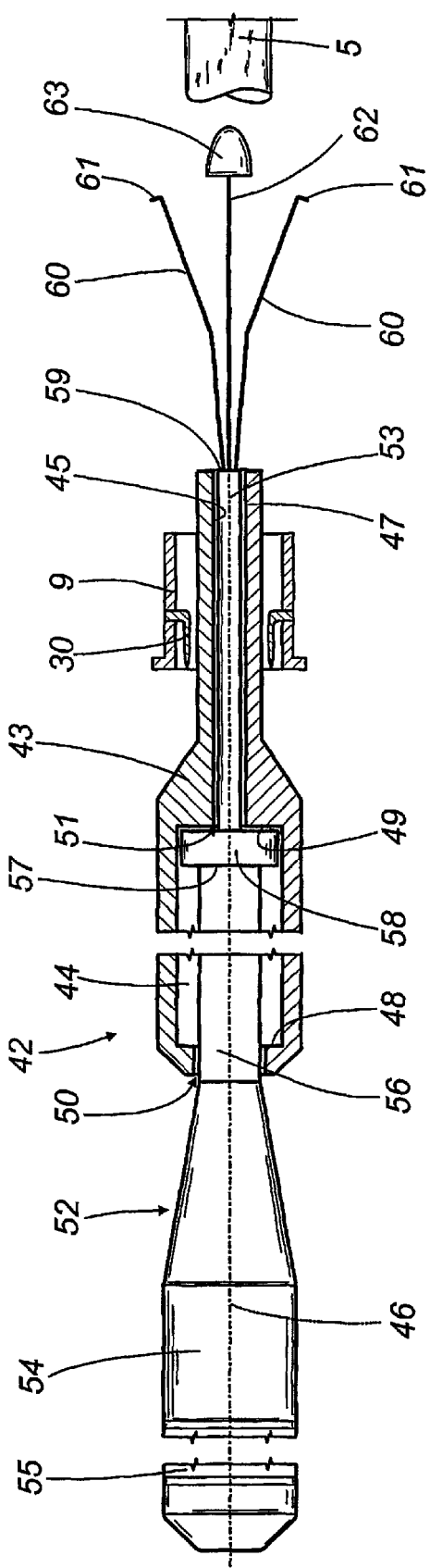
FIG. 3 is a schematic assembly view with some parts in cross-section and some parts cut away for greater clarity, of an embodiment of the apparatus made in accordance with the present invention.

As illustrated in FIG. 3, the apparatus 10 also comprises an applicator device 42 for applying and positioning the connecting elements 8 and 9 on the respective end portions 4 and 5.

In particular, FIG. 3 illustrates the device 42 on which the element 9 is removably pre-fitted, although the following description also applies to the element 8, since the device 42 may be used for either of the elements 8 and 9.

The device 42 comprises a hollow body 43, the inside of which forms two cylindrical chambers 44 and 45 which are intercommunicating and extend symmetrically about a shared longitudinal axis 46.

The chamber 45 is smaller in diameter than the chamber 44 and is delimited by a tubular portion 47 of the body 43 on which the element 9 may be pre-mounted in such a way that it slides and is removable, with the hooks 30 facing the portion 47.

The chamber 44 is axially delimited by two walls 48 and 49 with respective through-holes 50 and 51, the hole 51 constituting an inlet into the chamber 45.

The device 42 also comprises a rod 52 connected in such a way that it can slide to the body 43, so that it runs longitudinally in both directions along the axis 46.

The rod 52 has an end portion 53 designed to run inside the chamber 45 through the hole 51, an end portion 54, opposite the portion 53, forming a grip 55 outside the body 43, and a middle portion 56 designed to run inside the chamber 44 through the hole 50.

At an end portion 57 facing the portion 53, the portion 56 is rigidly connected to a ring-shaped flange 58 designed to run inside the chamber 44 and along the axis 46, between a first, back position (FIG. 4), in which the flange 58 makes contact with the wall 48, and a second, forward position (FIG. 3), in which the flange 58 makes contact with the wall 49.

In the direction of the axis 46, the length of the portion 53 is equal to that of the chamber 45 and the end 59 of the portion opposite the portion 56 is connected to a plurality of elastic rods 60, which diverge from the axis 46 substantially according to the side surface of a cone whose vertex is at the end 59.

At the end opposite the end 59, each rod 60 is connected to a hook 61, and each rod is designed to assume an infinite number of intermediate elastic deformation configurations between a position which is distanced from the axis 46 (FIG. 3), in which the rod 60 substantially lies on the above-mentioned conical side surface, and a position close to the axis 46 (FIG. 4), in which the rod 60 is designed to run in the chamber 45.

The end 59 of the portion 53, as well as the rods 60, is connected to another rod 62, which extends centrally to the rods 60 along the axis 46 and has a rounded nosepiece 63 at the end opposite the end 59.

The rod 62 is longer than the rods 60 by an amount which leaves the hooks 61 behind the nosepiece 63 when the rods 60 are in the above-mentioned position close to the axis 46. In this position the hooks 61 diverge from the rod 62.

Operation of the apparatus 10 includes an initial step in which each end portion 4, 5 is fitted with the connecting element 8, 9, and a final step in which the connecting elements 8, 9 are fixed to one another using the above-mentioned locking means 37.

The initial step is carried out with the aid of the applicator device 42, using methods which, for the purpose of brevity, relate only to the element 9 in the description which follows.

With the flange 58 in the above-mentioned back position (FIG. 4), the rods 60 and the rod 62 are arranged in a bundle inside the chamber 45.

In this condition, the hooks 61 are gathered behind the nosepiece 63, which is substantially in contact with the portion 47 of the body 43.

At this point, the portion 47 is inserted in the portion 5 by a given length, in particular three millimetres. During this operation, the nosepiece 63 acts as an element which protects the portion 5 from the hooks 61.

A further movement of the flange 58 to the above-mentioned forward position causes the rods 60 and 62 to leave the chamber 45 and consequent elastic widening of the rods 60, by means of which the hooks 61 engage and hold the inner wall of the portion 5 (FIG. 5).

The connecting element 9 is then run outside the portion 5 beyond the end edge 7 by a given distance, in particular three millimetres (FIG. 6). It is then run in the opposite direction, that is to say, towards the grip 55, so that the fixing hooks 30 engage in the portion 5.

The flange 58 is then moved to its back position and the hooks 61 release the portion 5.

The portion 47 is then removed from the portion 5.

Again, the nosepiece 63 acts as an element which protects the portion 5 from the hooks 61.

It should be noticed that, as well as axially holding the portion 5, the rods 60 and hooks 61 are designed to support the portion 5 from the inside towards the outside during said connection of the element 9.

Once the element 9 is connected to the portion 5, the device 42 is put away and a scalpel (not illustrated) is used to cut the portion 5 flush with the edge 28 of the element 9.

Following this operation, the end edge 7 of the portion 5 is perfectly coplanar with and adjacent to the edge 28 of the element 9.

Then after repeating the above-mentioned steps for portion 4 and for the connecting element 8, the elements 8 and 9 are brought together and locked using the locking tooth 41.

Once locked, the axes 12 and 25 of the elements 8 and 9 are aligned and the elements are pressed against one another along the edges 15 and 28 by the elastic force exerted by the coupling 38 according to the axes 12 and 25.

Thanks to the tubular bodies 11 and 24 and the hooks 17 and 30, the elements 8 and 9 evenly calibrate the portions 4 and 5, restoring the shared original calibre.

The above, together with the fact that the end edges 6 and 7 of the portions 4 and 5 are completely free and disengaged from the elements 8 and 9, allows the corresponding layers of the two portions 4 and 5 to be fitted together in a configuration of close and total reciprocal contact. In other words, with anastomosis performed according to the method described above, no point of each of the layers of an edge 6, 7 remains isolated from the matching point of the corresponding layer of the other edge 6, 7.

It should be emphasised that the elasticity of the bodies 11 and 24 and the flanges 23 and 36 allows the connecting elements 8 and 9 to adapt elastically to any variations in the calibre of the respective portions 4 and 5 of the vessel 3.

Figure 7:
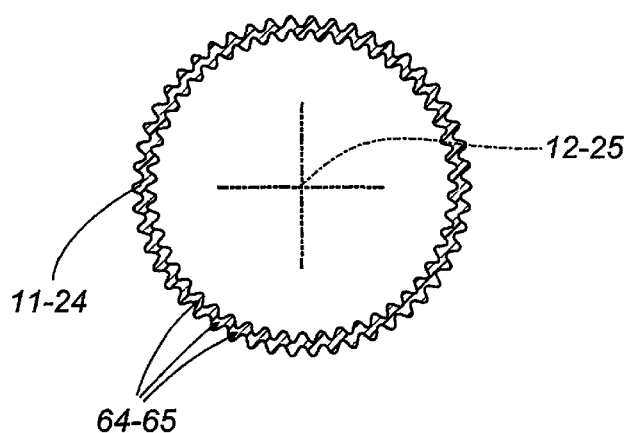
FIG. 7 is a transversal section of another embodiment of the portion illustrated in FIG. 1.

In an alternative embodiment illustrated in FIG. 7, although the bodies 11 and 24 still have a substantially cylindrical tubular shape, they have a plurality of longitudinal concertina-style folds 64, 65, evenly distributed about the axes 12 and 25. Although not illustrated, the folds 64, 65 extend on the flanges 23 and 36.

The folds 64, 65 give the connecting elements 8 and 9 more transversal (radial) elasticity for improved automatic elastic adaptation to any variations in the calibre of the vessel 3. In this case it is not essential, but it is preferable for the bodies 11 and 24 and the flanges 23 and 36 to be made of an elastic material.

In an alternative embodiment not illustrated of the connecting elements 8 and 9, the hooks 17 and 30 are integrated, in a single body, with the tubular support bodies 11 and 24.

Figure 8:
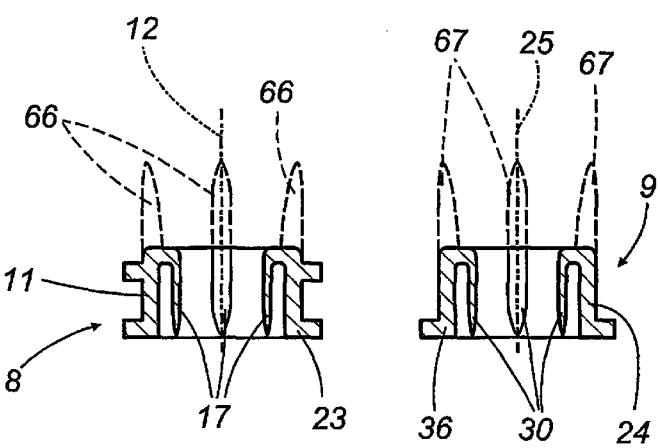
FIG. 8 illustrates another embodiment of the portion in FIG. 1.

In the alternative embodiment of the connecting elements 8 and 9 illustrated in FIG. 8, the hooks 17 and 30 are obtained by clinching or bending the longitudinal tabs 66, 67 of the tubular bodies 11 and 24. Said tabs 66, 67, illustrated with a dashed line in FIG. 8, are 2–3 tenths long in the direction of the axes 12 and 25 and are clinched, that is to say, folded, inside the tubular bodies 11 and 24 towards the flanges 23 and 36.

Figure 9:
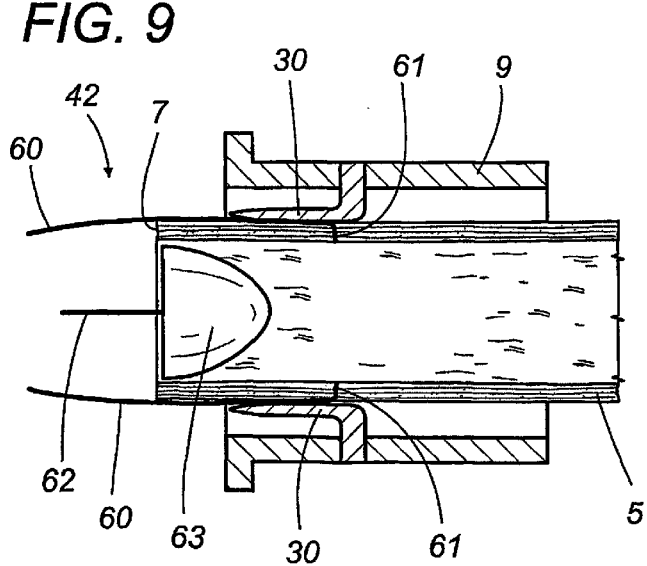
FIG. 9 illustrates another embodiment of the apparatus in FIG. 3.

In the alternative embodiment of the applicator device 42 illustrated in FIG. 9, the hooks 61 of the rods 60 face the rod 62, that is to say, they converge on the latter.

Moreover, the rod 62 is shorter than the rod 60 by a distance which allows the hooks 61 to surround and close over the tip of the nosepiece 63 when the rods 60 are in the above-mentioned position close to the axis 46.

In this case, use of the applicator device 42 differs from that described above. The portion 47 is not inserted in the portion 5 and the flange 58 is kept in its forward position during insertion of the nosepiece 63 in the portion 5.

Subsequent sliding of the flange 58 towards its back position allows the rods 60 to move towards the rod 62 and consequent external engagement of the portion 5 by the hooks 61.

The connecting element 9 is then run on the rods 60 until it reaches the portion 5.

Subsequent sliding in both directions of the element 9 on the portion 5 is carried out using the same methods as described above in order to engage the fixing hooks 30 in the portion 5.

It should be noticed that the rods 60, being positioned between the portion 5 and the element 9 during the sliding of the latter along the rods 60, prevent any eversion of the portion 5 from obstructing the sliding of the element 9 on the portion 5.

Obviously, the description referring to the vessel 3 also applies to any type of duct requiring an anastomosis technique.

Finally, it should be noticed that the steps described above, involving relatively simple movements between the various parts, may be advantageously performed by either a surgeon or a robot.

What is claim is:

1. An apparatus for anastomosis between a first and a second part (1, 2) of a vessel (3) or of a duct (3), the first and second parts (1, 2) respectively having a first and second end portion (4, 5) delimited by free end edges (6, 7), the apparatus (10) being characterised in that it comprises first connecting means (8) which are shaped to match and may be positioned on the first end portion (4) in order to engage the first end portion (4) with the exception of the free end edge (6), second connecting means (9) which are shaped to match and may be positioned on the second end portion (5) in order to engage the second end portion (5) with the exception of the free end edge (7), and connecting means (23, 36, 37) for connecting and fixing together the first and second connecting means (8, 9) in a position (P) in which they are attached to one another and in which the end edges (6, 7) meet in a configuration of close and total reciprocal contact, the first and second connecting means respectively comprising first and second fixing means for the first and second end portions, the first and second fixing means each comprising a plurality of first hooks designed to perforate and retain, respectively, the first and second end portions.

2. The apparatus according to claim 1, characterised in that the first and second connecting means (8, 9) respectively comprise a first and second tubular connecting element (11, 24), the first and second connecting elements (11, 24) being designed to engage the first and second end portion (4, 5) on the outside of the first and second end portions (4, 5).

3. The apparatus according to claim 2, characterised in that the first and second connecting elements (11, 24) are delimited on the inside by substantially cylindrical surfaces (13, 26).

4. The apparatus according to claim 3, characterised in that, for each of the first and second connecting elements, the first hooks are supported by the first and second connecting elements (11, 24).

5. The apparatus according to claim 4, characterised in that, for each of the first and second connecting elements (11, 24), the first hooks (17, 30) are evenly distributed in a ring shape inside the first and second connecting elements (11, 24).

6. The apparatus according to claim 2, characterised in that the connecting means comprise a first flange extending outside the first connecting element, the first flange being designed to be placed axially flush with the free end edge; a second flange extending outside the second connecting element, the second flange being designed to be placed axially flush with the free end edge; and releasable locking means for locking the first and second flanges in a position in which they are connected to one another and in which the end edges meet in a configuration of close and total reciprocal contact.

7. The apparatus according to claim 6, characterised in that the releasable locking means (37) are supported by at least one of the first and second connecting elements (11, 24).

8. The apparatus according to claim 7, characterised in that the releasable locking means (37) comprise an elastic coupling (38) supported by at least one of the first and second connecting elements (11, 24).

9. The apparatus according to claim 8, characterised in that the releasable locking means (37) comprise a ring-shaped tooth (41) which can be elastically deformed, being supported by the elastic coupling (38).

10. Apparatus according to claim 2, wherein tubular elements (11) and (24) have a plurality of longitudinal concertina-style folds (64), (65).

11. Apparatus according to claim 10, wherein the folds (64, 65) extend on flanges (23) and (36) of said elements (11, 24).

12. Apparatus according to claim 2, wherein the connecting elements (8) and (9), the hooks (17) and (30) are integrated in a single body with said tubular elements (11) and (24).

13. The apparatus according to claim 1, characterised in that the first and second connecting means and the connecting means for connecting and fixing together the first and second connecting means are made of a bio-compatible material.

14. The apparatus according to claim 13, characterised said material is a bio-absorbable material.

15. The apparatus according to claim 1, characterised in that it comprises applicator means for applying and positioning the first and second connecting means on the first and second end portions; said first and second connecting means being removably pre-mountable on the applicator means.

16. The apparatus according to claim 15, characterised in that the applicator means (42) comprise first and second support means (43, 52) which are slidably connected to one another; the first support means (43) being designed to support the first and second connecting means (8, 9) in such a way that they can slide and be removed, and the second support means (52) being connected to gripping and fixing means (60, 61) designed to engage and hold the first and second end portions (4, 5).

17. The apparatus according to claim 16, characterised in that the first support means (43) comprise a first tubular support element (47) designed to support the first and second connecting means (8, 9) inside the first and second connecting means (8, 9).

18. The apparatus according to claim 16, characterised in that the gripping and fixing means comprise a plurality of second hooks designed to engage and hold the first and second end portions inside the first and second end portions.

19. The apparatus according to claim 17, characterised in that the second support means (52) comprise a second support element (53, 56) mounted in such a way that it slides inside the first support element (47).

20. The apparatus according to claim 16, characterised in that the gripping and fixing means comprise a plurality of second hooks designed to engage and hold the first and second end portions outside the first and second end portions.

* * * * *

UNITED STATES PATENT AND TRADEMARK OFFICE
CERTIFICATE OF CORRECTION

PATENT NO. : 6,736,824 B2
DATED : May 18, 2004
INVENTOR(S) : Enzo Borghi

It is certified that error appears in the above-identified patent and that said Letters Patent is hereby corrected as shown below:

Title page,
Item [86], PCT NO.: this application claims priority to -- PCT/IB01/00490 -- filed -- 26 March 2001. --

Signed and Sealed this

Thirteenth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,736,824 B2
DATED : May 18, 2004
INVENTOR(S) : Enzo Borghi

It is certified that error appears in the above-identified patent and that said Letters Patent is hereby corrected as shown below:

Title page,
Item [30], References Cited, Foreign Application Priority Data:
should read -- March 28, 2000 [IT] Italy BO 2000A 000169 --.

Signed and Sealed this

Seventh Day of September, 2004

JON W. DUDAS
*Director of the United States Patent and Trademark Office*